(12) United States Patent
Van Den Boogaard et al.

(10) Patent No.: US 9,255,244 B2
(45) Date of Patent: Feb. 9, 2016

(54) BIOREACTOR

(75) Inventors: Juergen Van Den Boogaard, Dransfeld (DE); Gerhard Greller, Goettingen (DE); Jens Ludwig, Juehnde (DE); Oscar-Werner Reif, Hanover (DE)

(73) Assignee: Sartorius Stedim Biotech GmbH (DE)

( * ) Notice: Subject to any disclaimer, the term of this patent is extended or adjusted under 35 U.S.C. 154(b) by 366 days.

(21) Appl. No.: 12/867,647

(22) PCT Filed: Feb. 12, 2009

(86) PCT No.: PCT/EP2009/000961
§ 371 (c)(1),
(2), (4) Date: Aug. 13, 2010

(87) PCT Pub. No.: WO2009/103450
PCT Pub. Date: Aug. 27, 2009

(65) Prior Publication Data
US 2011/0003374 A1 Jan. 6, 2011

(30) Foreign Application Priority Data

Feb. 21, 2008 (DE) .......................... 10 2008 010 427

(51) Int. Cl.
C12M 1/00 (2006.01)
C12M 3/00 (2006.01)
C12M 1/06 (2006.01)
B01F 7/16 (2006.01)
B01F 15/00 (2006.01)
C12M 1/12 (2006.01)
F16C 33/76 (2006.01)

(52) U.S. Cl.
CPC .............. *C12M 27/02* (2013.01); *B01F 7/1695* (2013.01); *B01F 15/0085* (2013.01); *B01F 15/00831* (2013.01); *C12M 23/26* (2013.01); *C12M 37/04* (2013.01); *F16C 33/76* (2013.01)

(58) Field of Classification Search
CPC ....... C12M 27/00; C12M 27/02; C12M 37/04
See application file for complete search history.

(56) References Cited

U.S. PATENT DOCUMENTS

| 4,379,846 | A | * | 4/1983 | Shkidchenko et al. .... 435/299.1 |
| 4,721,312 | A | | 1/1988 | Hornberger |
| 5,211,406 | A | | 5/1993 | Katzensteiner |
| 5,364,245 | A | | 11/1994 | Kriehn et al. |
| 5,509,667 | A | | 4/1996 | Klein et al. |

(Continued)

FOREIGN PATENT DOCUMENTS

| DE | 33 13 081 | 10/1986 |
| DE | 198 08 280 | 9/1999 |

(Continued)

*Primary Examiner* — Nathan Bowers
(74) *Attorney, Agent, or Firm* — Gerald E. Hespos; Michael J. Porco; Matthew T. Hespos

(57) ABSTRACT

A bioreactor (1) having a container (2), a shaft housing (3) for guiding a shaft (5) through a wall (7), a stirrer (6) connected to the shaft (5) in the interior (9) of the container (2), and a drive (4) arranged outside the container (2) and connectable to the shaft (5). The shaft (5) is mounted in the shaft housing (3) via at least one ball bearing (23) and is sealed in relation to the shaft housing (3) by at least one seal (11, 20). The seal (11, 20) is configured as a radial shaft seal (28) having two sealing lips (30, 31) that are arranged one behind the other in the longitudinal direction of the shaft (5) and are able to run on the shaft (5) without lubricant.

14 Claims, 4 Drawing Sheets

(56) References Cited

U.S. PATENT DOCUMENTS

| | | |
|---|---|---|
| 6,357,751 B1 | 3/2002 | Rentschler |
| 2002/0074734 A1 | 6/2002 | Reinhardt et al. |
| 2005/0001384 A1 | 1/2005 | Reinhard |
| 2005/0239199 A1 | 10/2005 | Kunas et al. |
| 2006/0280028 A1 | 12/2006 | West et al. |
| 2010/0233795 A1* | 9/2010 | Mayer .................. 435/289.1 |

FOREIGN PATENT DOCUMENTS

| | | |
|---|---|---|
| DE | 103 19 821 | 11/2004 |
| DE | 10 2004 025 355 | 2/2006 |
| EP | 0 191 894 | 7/1989 |
| EP | 1 156 242 | 11/2005 |
| WO | 2005/104706 | 11/2005 |
| WO | 2005/108546 | 11/2005 |

* cited by examiner

BIOREACTOR

BACKGROUND OF THE INVENTION

1. Field of the Invention

The invention relates to a bioreactor having a container, a shaft housing for guiding a shaft through a wall, a stirrer connected to the shaft in the interior of the container, and a drive arranged outside the container and connectable to the shaft, said shaft being mounted in the shaft housing via at least one ball bearing and being sealed in relation to the shaft housing by at least one seal.

2. Description of the Related Art

Bioreactors having a container with a flexible wall are being increasingly used, particularly as disposable bioreactors, in pharmacy and biotechnology.

US 2006/0280028 A1 discloses a bioreactor having a container with a flexible wall, through which wall a shaft is guided in order to drive a stirrer arranged in the interior of the container. A shaft housing is connected to the flexible wall via a sealing flange. The shaft is mounted in the shaft housing via two ball bearings. The shaft has a flat radial sealing collar, which is arranged in a recess of the shaft housing. The outer annular end face directed away from the interior of the container is sealed in relation to a bottom surface of the recess by a lip seal. The inner annular end face of the collar, directed toward the interior of the container, is sealed in relation to the locked floor part of the shaft housing by two coaxially arranged lip seals.

A disadvantage of the above is that the structure of the shaft housing, in conjunction with the seals, is quite complicated and cost-intensive and also takes up quite a large volume.

Moreover, US 2005/0239199 A1 discloses a bioreactor having a container with a flexible wall, in which container a shaft is guided rotatably through the flexible wall into the interior of the container by way of a shaft housing connected to the flexible wall. In the shaft housing opening directed toward the interior, the shaft is guided by a radially protruding annular disk which is arranged in said opening and which is sealed in relation to a recess of the shaft housing by two coaxially arranged lip seals.

This device also has the abovementioned disadvantages.

EP 1 156 242 A2 discloses a radial shaft seal with two sealing lips, in which the sealing lip lying on the hydraulic side is pressed by an annular helical spring onto the shaft that is to be sealed. A disadvantage of this is that these seals are designed as seals running in hydraulic liquid, or at least as lubricated seals, in which the space between the sealing lips is used as a lubricant depot.

The object of the present invention is therefore to make available a bioreactor having a container in which the shaft is guided through a wall, which is flexible for example, by way of a compact structure and in a simple and inexpensive manner and yet in a liquid-tight and gas-tight manner.

SUMMARY OF THE INVENTION

The object is achieved by a seal which is configured as a radial shaft seal having two sealing lips that are arranged one behind the other in the longitudinal direction of the shaft and are able to run on the shaft without lubricant.

It has surprisingly been found that when using a radial shaft seal with two lips, as are known for the sealing of annular gaps in relation to rotating shafts between a pressurized hydraulic side and an atmospheric side in wet running or with lubrication of the sealing lip, in the present case permit a sufficient gas seal and liquid seal even when the sealing lips run without lubricant. With unlubricated running, it is possible to dispense with lubricants that contaminate the reactor contents or react with the reactor contents. By using the at least one radial shaft seal, it is possible to dispense with a special disk-shaped sealing collar on the shaft. The shaft housing with the shaft can thus have a simple, cost-effective and compact design.

According to a preferred embodiment of the invention, the radial shaft seal has, in the direction toward the interior of the container, a closed end face which merges in the radial direction into a sealing lip configured as a protective lip, and the radial shaft seal has, in the direction toward the drive on the outside, a sealing lip which a spring ring presses sealingly against the shaft surface. In this way, the protective lip known from the use of a radial shaft seal in hydraulics is placed not on the atmospheric side but on the pressure side, i.e. the radial shaft seal is turned through 180° in relation to its normal mode of use and yet still provides the desired gas-tight and liquid-tight seal. The first sealing lip formed as protective lip holds back particles from the interior of the container and protects the second sealing lip against particles impairing the seal.

According to another preferred embodiment of the invention, a second seal is arranged adjacent to the first seal in the longitudinal direction of the shaft. By virtue of the fact that the two seals are not arranged coaxially with respect to each other in the radial direction but are instead arranged one behind the other in the axial direction, the compact nature of the shaft housing is substantially maintained. The sealing action of the two radial shaft seals arranged one behind the other is thereby increased.

The free end of the shaft directed away from the stirrer or the interior of the container can be coupled to a drive shaft of a motor of the drive. The free end of the shaft can be coupled to the drive shaft via a chuck.

According to another preferred embodiment of the invention, the shaft is fixed in its longitudinal direction via the seat of the ball bearing, and the ball bearing is arranged in a recess of the shaft housing and is secured in its position by a circlip arranged in an annular groove of the shaft housing.

Particularly when the bioreactor is used as a disposable bag, it is also possible for the shaft housing including ball bearing, shaft and shaft seal to be made of plastic.

Further features of the invention will become clear from the following detailed description and from the attached drawings in which preferred embodiments of the invention are illustrated by way of example.

DETAILED DESCRIPTION OF THE PREFERRED EMBODIMENTS

Figure 1:
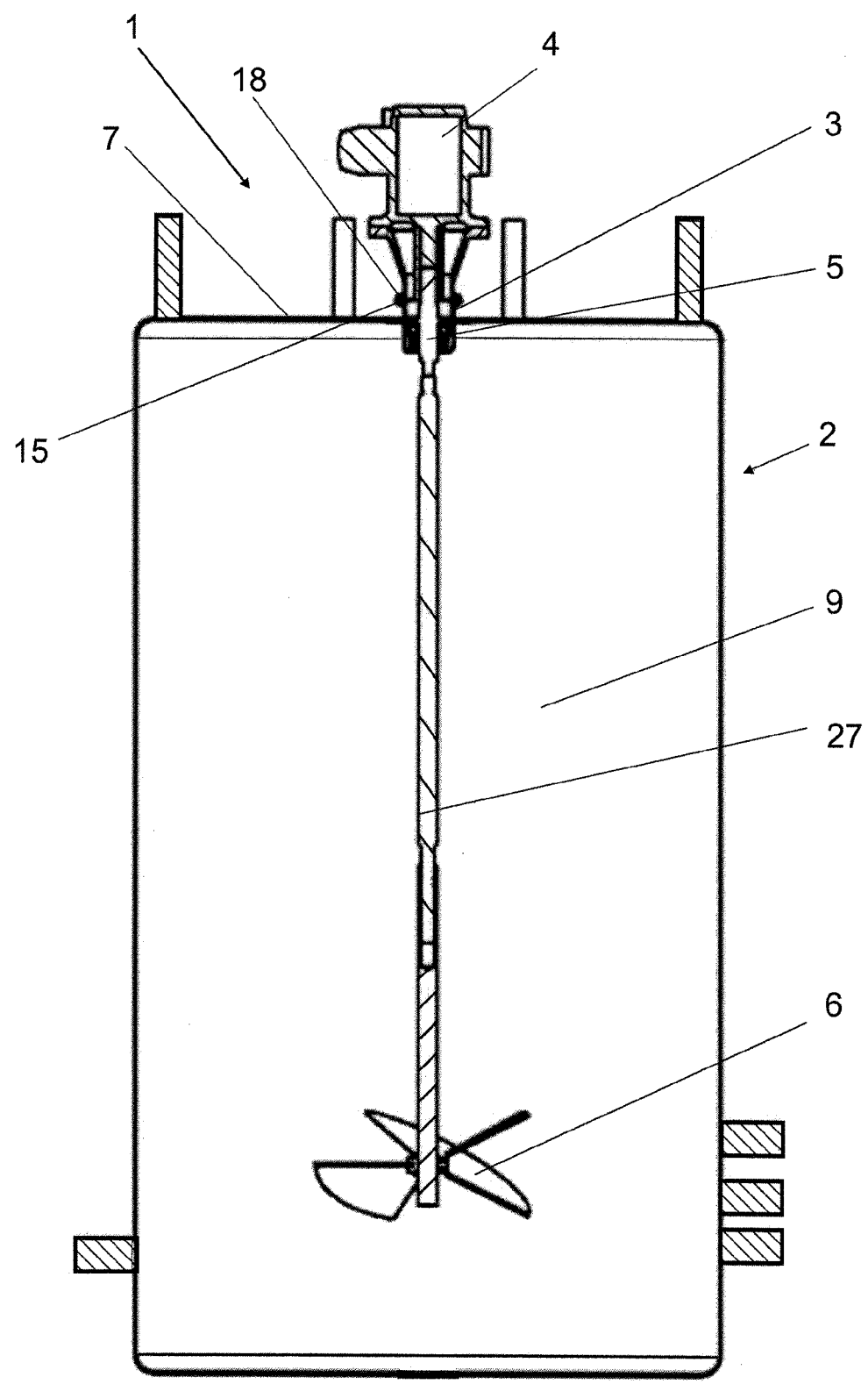
FIG. 1 shows a schematic side view of a bioreactor.
Figure 2:
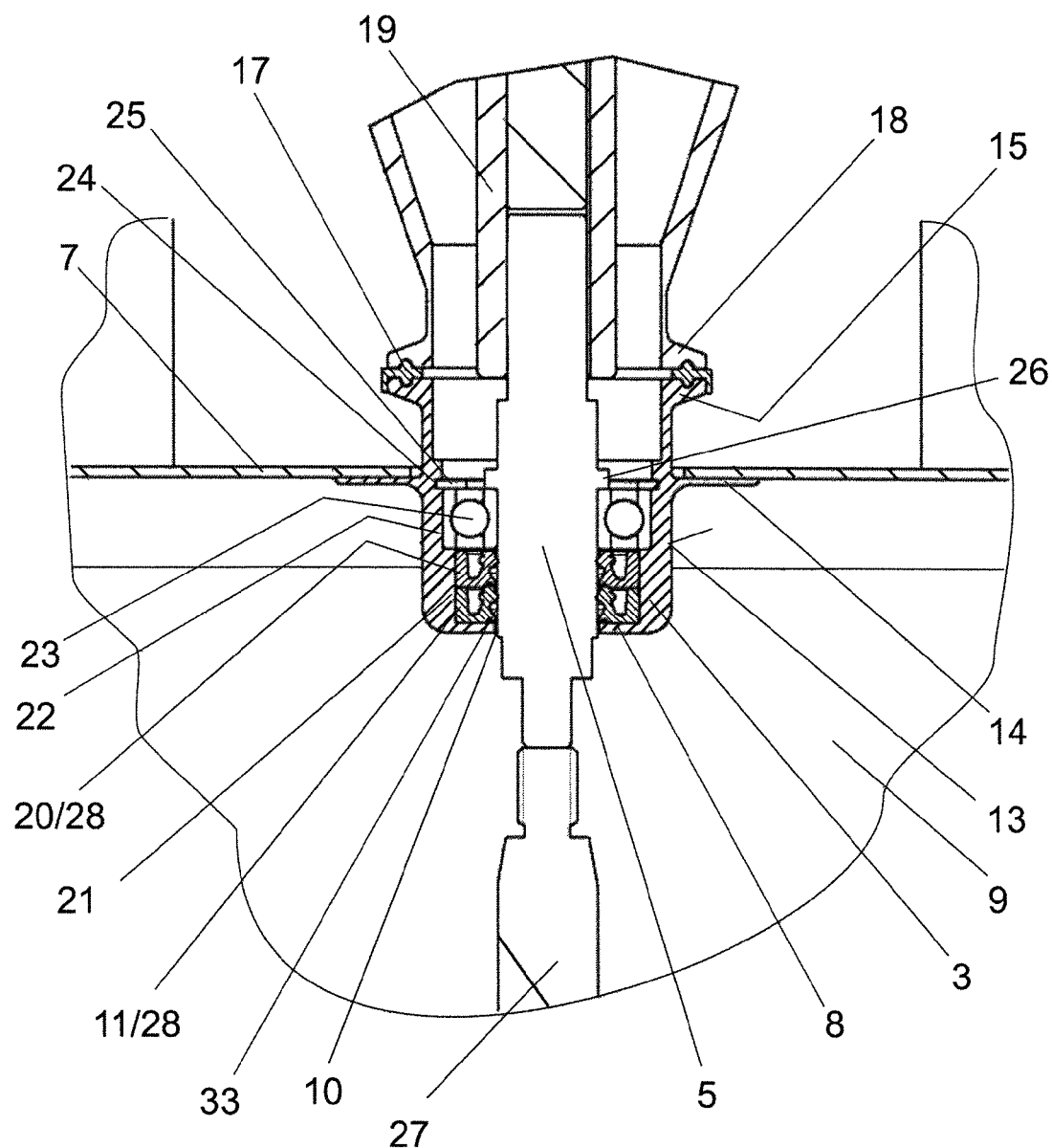
FIG. 2 shows an enlarged and sectional side view of the shaft housing from FIG. 1.
Figure 3:
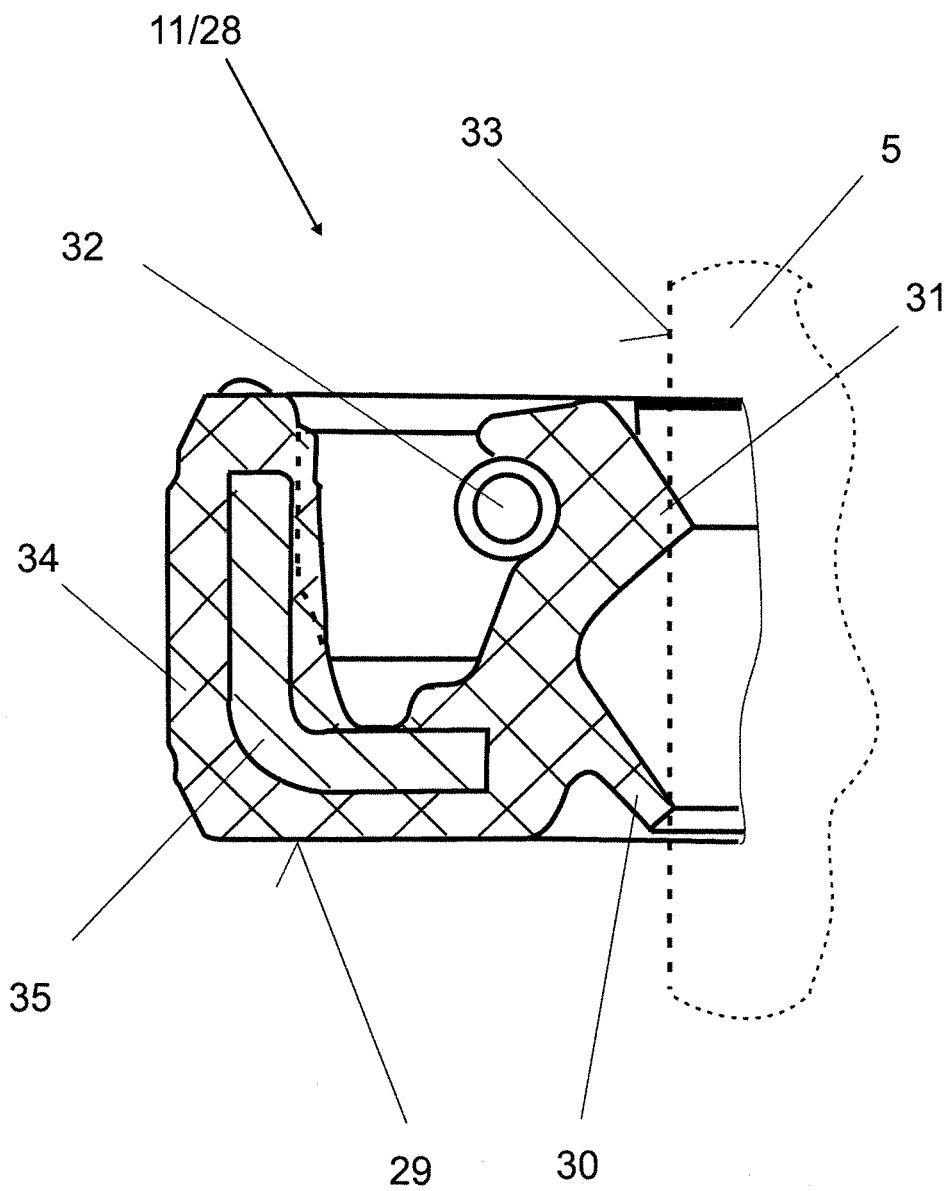
FIG. 3 shows a sectional side view of a shaft seal.
Figure 4:
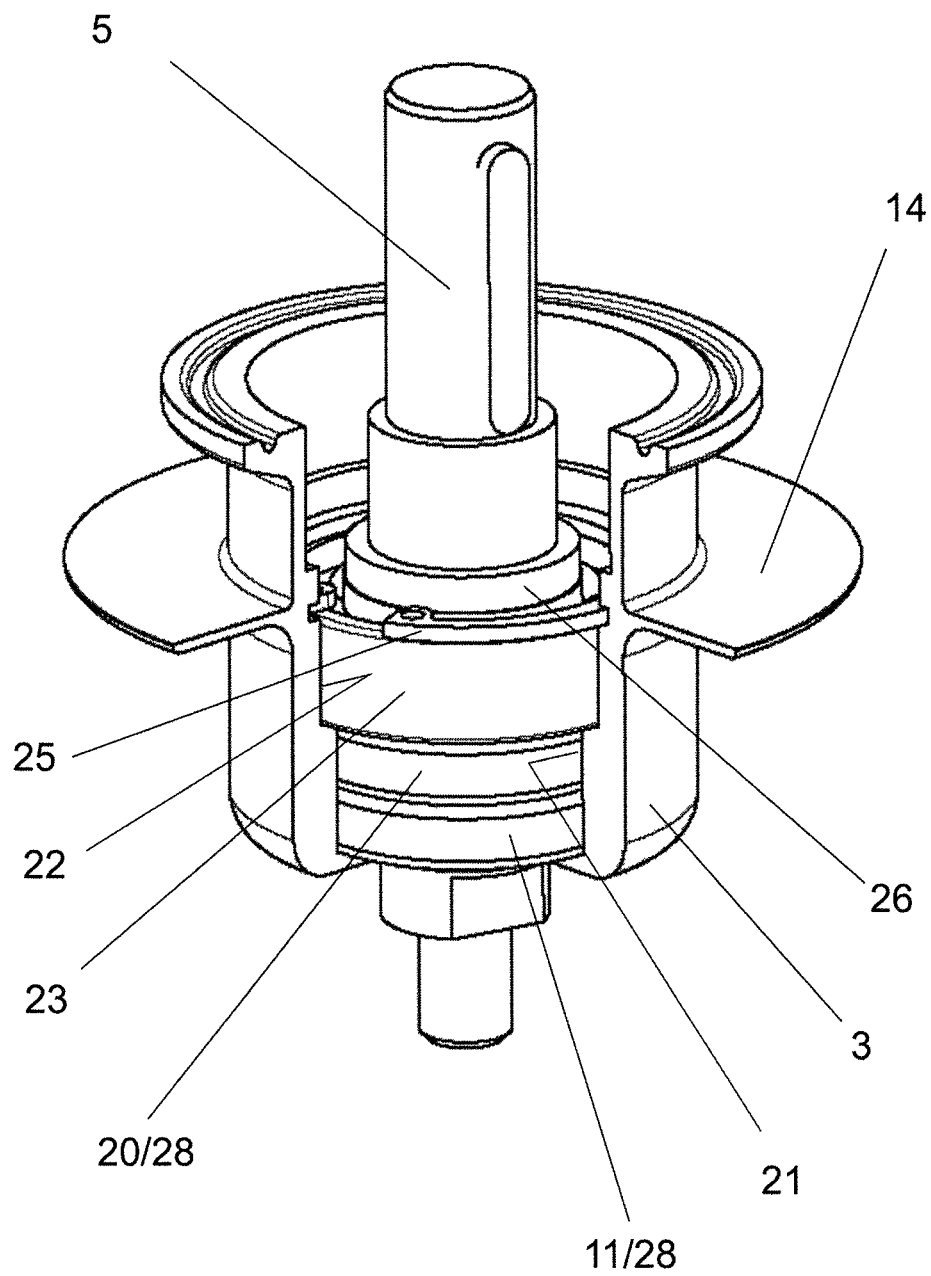
FIG. 4 shows a perspective view of a shaft housing.

A bioreactor 1 basically comprises a container 2, a shaft housing 3, a drive 4, a shaft 5 and a stirrer 6.

The container 2 has a flexible wall 7 which at the top in the vertical direction is securely connected to the shaft housing 3 for passage of the shaft 5. The shaft housing 3 is pot-shaped and its lower part, comprising a floor 8, protrudes into an interior 9 of the container 2. The floor 8 has a through-opening 10 for the shaft 5 and forms a support bearing for a first seal 11, which bears with its end face 12 on the floor 8. The shaft housing 3 has a cylindrical outer wall 13 with a radially extending, flat collar 14 which is connected to the adjacent flexible wall 7 of the container 2. The connection can be made, for example, by adhesive bonding or ultrasonic welding.

At its upper edge directed away from the floor 8, the shaft housing 3 has a flange 15 with an annular groove 16 for receiving a flange seal 17. The drive 4 can be flanged onto the flange 15 with a flange 18. For connection to the shaft 5, the drive 4 has a coupling 19. A second seal 20 is arranged adjacent to the first seal 11 in the longitudinal direction of the shaft 5. The two seals 11, 20 are arranged in a lower recess 21 of the shaft housing 3, which recess 21 is delimited vertically at the bottom by the floor 8. A second recess 22 for receiving a ball bearing 23 is arranged above the lower recess 21 in the shaft housing 3. Adjacent to the second recess 22, the shaft housing 3 has an annular groove 24 in which a spring ring or circlip 25 is fitted for fixing the ball bearing 23. The shaft 5 has a circumferential collar 26, which serves as abutment for the ball bearing 23 arranged fixedly thereon. The shaft 5 is thus fixed in its longitudinal direction on the shaft housing 3 by the ball bearing 23 and the circlip 25. The stirrer 6 is connected by its shank 27 to the shaft 5 driving it. The shank 27 can be configured in several parts to permit adaptation to different container sizes. The seals 11, 20 are configured as a radial shaft seal 28. The radial shaft seal 28 has the end face 29 located at the bottom in the vertical direction. In the radial direction, the end face 29 merges into a first sealing lip 30 which, in hydraulic applications, forms a kind of sealing protective lip. The first sealing lip 30 is adjoined at the top in the vertical direction by a second sealing lip 31, which is pressed sealingly against the shaft surface 33 of the shaft 5 by a spring ring 32. The end face 29 and the outer wall 34 of the radial shaft seal 28 directed toward the shaft housing 3 and extending parallel to the shaft 5 have, offset toward the inside, a cupped reinforcement 35.

The invention claimed is:

1. A bioreactor (1) comprising: a flexible container (2) with a wall (7) and an interior (9), a shaft (5) extending through the wall (7), a stirrer (6) connected to the shaft (5) in the interior (9) of the container (2), a drive (4) arranged outside the container (2) and connectable to the shaft (5), a shaft housing (3) mounted to the wall (7), the shaft housing (3) having a floor (8) disposed in the interior (9) of the container (2), the floor (8) surrounding the shaft (5) and extending out from the shaft (5), a tubular outer wall (13) surrounding and spaced out from the shaft (5) and a flat collar (14) extending out from the outer wall (13) and connected to the wall (7) of the container (2), a first recess (21) formed in the shaft housing (3) adjacent the floor (8) and a second recess (22) adjacent the first recess (21), the second recess (22) being cross-sectionally larger than the first recess (21) to define a step therebetween, at least one ball bearing (23) disposed in at least one track supported on the step in the second recess (22) of the shaft housing (3) for permitting rotation of the shaft (5) relative to the shaft housing (3) and at least one seal (11, 20) in first recess (21) of the housing (3) and supported on the floor (8) with all of the seal (11, 20) being between the floor (8) and the ball bearing (23), the seal (11, 20) being configured as a radial shaft seal (28) having an outer surface opposed to the outer wall (13) and an inner surface with first and second sealing lips (30, 31) that are arranged one behind the other in a longitudinal direction of the shaft (5), the sealing lips (30, 31) sealingly engaging the shaft (5) with no lubricant therebetween, the seal (11, 20) having a closed end face (29) at an end of the seal (11, 20) toward the interior (9) of the container (2), the closed end face (29) merging in a radial direction into the first sealing lip (30), with the first sealing lip (30) being configured as a protective lip, the second sealing lip (31) being between the first sealing lip (30) and the ball bearing (23), and a spring ring (32) radially outward of the second sealing lip (32) and pressing in the second sealing lip (31) sealingly against the shaft (5), a circumferential collar (26) extending out from the shaft (5) and engaging an end of the at least one track of the ball bearing (23) opposite the at least one seal (11, 20) and a spring ring or circlip (25) engaged in an annular groove in the shaft housing (3) and engaging the end of the at least one track of the ball bearing (23) opposite the at least one seal (11, 20).

2. The bioreactor as claimed in claim 1, wherein the at least one seal (11, 20) is a first seal (11) and wherein the bioreactor further comprises a second seal (20) arranged adjacent to the first seal (11) in the longitudinal direction of the shaft (5).

3. The bioreactor as claimed in claim 1, wherein the end face (29) and an outer wall (34) of the radial shaft seal (28) directed toward the shaft housing (5) and extending parallel to the shaft (5) has a cupped reinforcement (35).

4. The bioreactor as claimed in claim 1, wherein the floor (8) of the shaft housing (3) has a through-opening (10) for the shaft (5), the floor (8) forming a support bearing for the at least one seal (11), which bears with an end face (12) on the floor (8).

5. The bioreactor as claimed in claim 4, wherein the outer wall (13) is substantially cylindrical and the flat collar (14) is connected to the wall (7) of the container (2) in the interior (9).

6. The bioreactor as claimed in claim 5, wherein the shaft housing (3) has a flange (15) at an upper end opposite the floor (8) and outside the container (2), the flange (15) being formed with an annular groove (16) for receiving a flange seal (17), and the drive (4) having a corresponding flange (18) flanged onto the flange (15).

7. The bioreactor as claimed in claim 1, wherein a free end of the shaft (5) directed away from the stirrer (6) is coupled to a motor of the drive (4).

8. The bioreactor as claimed in claim 7, wherein the free end of the shaft (5) can be coupled to the drive (4) via a coupling (19).

9. The bioreactor of claim 1, wherein the at least one track comprises inner and outer circumferential tracks, the circumferential collar (26) extending out from the shaft (5) engaging the end of the inner circumferential track opposite the at least one seal (11, 20), and the spring ring or circlip (25) engaging the end of the outer circumferential track opposite the at least one seal (11, 20).

10. A bioreactor (1) comprising:
a flexible container (2) having a wall (7) defining an interior (9) within the container (2);
a shaft housing (3) having a collar (14) secured to the wall (7) and disposed in the interior (9) of the container (2), a cylindrical side wall (13) extending from the collar (14) and into the interior of the container (2), a floor (8) extending in from an end of the outer wall (13) opposite the collar (14), the floor (8) having a central opening (10), a first recess (21) formed in the shaft housing (3) adjacent the floor (8) and a second recess (22) adjacent the first recess (21), the second recess (22) being cross-sectionally larger than the first recess (21) to define a step therebetween;
a shaft (5) having an inner end in the interior (9) of the container (2), an intermediate portion passing through the central opening (10) of the floor (8) of the shaft housing (3) and an outer end projecting out of the container (2);

at least one ball bearing (23) disposed in at least one track in the second recess (22) of the shaft housing (3) and supported on the step between the second recess (22) and the step (21); and at least one seal (28) in the first recess (21) of the shaft housing (3) with all of the seal (28) being between the floor (8) and the ball bearing (23) and surrounding the shaft (5), the seal (28) having an outer surface abutting the side wall (13) of the shaft housing (3), a closed end face (29) abutting and supported on the floor (8) and an inner surface having first and second sealing lips (30, 31) arranged one behind another in a longitudinal direction of the shaft (5) and biased against the shaft (5) with no lubricant between the seal (28) and the shaft (5), the closed end face (29) merging in a radial direction into the first sealing lip (30), with the first sealing lip (30) being configured as a protective lip, the second sealing lip (31) being between the first sealing lip (30) and the ball bearing (23), and a spring ring (32) radially outward of the second sealing lip (32) and pressing in the second sealing lip (31) sealingly against the shaft (5)

a circumferential collar (26) extending out from the shaft (5) and engaging an end of the at least one track of the ball bearing (23) opposite the at least one seal (11, 20) and a spring ring or circlip (25) engaged in an annular groove in the shaft housing (3) and engaging the end of the at least one track of the ball bearing (23) opposite the at least one seal (11, 20).

11. The bioreactor of claim 10, wherein the shaft housing (3) has a portion extending exteriorly of the container (2) and connected to a drive (4) for driving the shaft (5).

12. The bioreactor of claim 10, wherein the seal (28) further includes a cupped reinforcement (35) embedded therein at a position outwardly of the spring ring (32).

13. The bioreactor of claim 10, wherein the at least one seal (28) comprises first and second seals (28), the first seal (28) abutting the floor (8) of the shaft housing (3) and the second seal (28) abutting a side of the first seal (28) opposite the floor (8).

14. The bioreactor of claim 10, wherein the at least one track comprises inner and outer circumferential tracks, the circumferential collar (26) extending out from the shaft (5) engaging the end of the inner circumferential track opposite the at least one seal (11, 20), and the spring ring or circlip (25) engaging the end of the outer circumferential track opposite the at least one seal (11, 20).

* * * * *